United States Patent
Kownacki

(10) Patent No.: US 7,178,529 B2
(45) Date of Patent: Feb. 20, 2007

(54) NOCTUMAL ORAL AIRWAY DILATOR

(75) Inventor: Charles D. Kownacki, Erie, PA (US)

(73) Assignee: Dental Appliance Investors, Inc., Erie, PA (US)

( * ) Notice: Subject to any disclaimer, the term of this patent is extended or adjusted under 35 U.S.C. 154(b) by 312 days.

(21) Appl. No.: 10/484,828

(22) PCT Filed: Jul. 25, 2001

(86) PCT No.: PCT/US01/23442

§ 371 (c)(1),
(2), (4) Date: Jan. 26, 2004

(87) PCT Pub. No.: WO03/011198

PCT Pub. Date: Feb. 13, 2003

(65) Prior Publication Data

US 2004/0177853 A1    Sep. 16, 2004

(51) Int. Cl.
*A61F 5/56* (2006.01)

(52) U.S. Cl. ............. 128/848; 128/859; 128/861; 602/902

(58) Field of Classification Search ............. 128/846, 128/848, 859–862; 601/902; 602/902; 433/6–8
See application file for complete search history.

(56) References Cited

U.S. PATENT DOCUMENTS

| 4,505,672 | A | * | 3/1985 | Kurz | 433/6 |
| 5,365,945 | A | * | 11/1994 | Halstrom | 128/848 |
| 5,462,066 | A | * | 10/1995 | Snyder | 128/848 |
| 5,570,704 | A | * | 11/1996 | Buzzard et al. | 128/848 |
| 6,055,986 | A | * | 5/2000 | Meade | 128/848 |

* cited by examiner

*Primary Examiner*—Michael A. Brown
(74) *Attorney, Agent, or Firm*—Richard K Thomson

(57) ABSTRACT

An oral appliance (20) includes first and second mouthpiece elements (22,32) each equipped with adjustable ribs (30,40) on an anterior portion (24) and ramp surfaces (28,38) on each of its posterior arms (26). The ribs (22,32) slope upwardly, front to back at a steeper angle than the ramp surfaces. Preferably, the ribs (22,32) and the ramps (28,38) surfaces have maximum height which define a ratio in the range of between 2 and 2½ to mimic the differential in mouth opening between incisors and molars. The appliance has a plurality of laterally extending protrusions (42,44,46) that are engaged by elastic bands (48) to exert a force which simultaneously pulls the wear's mandible forward and biases the lower mouthpiece toward the upper mouthpiece. Adjustable ribs extend laterally to permit relative movement of the two mouthpiece elements to eliminate the buildup of tension in the wearer's jaw.

19 Claims, 3 Drawing Sheets

NOCTUMAL ORAL AIRWAY DILATOR

BACKGROUND AND SUMMARY OF THE INVENTION

The present invention is directed to an oral appliance for use in treatment of snoring and sleep apnea. More particularly, the present invention is directed to a pair of separate mouthpieces with ease of adjustability and which are designed to accommodate the differential in movement between the molars and incisors.

Typically, snoring is caused by the relaxation of the muscles in the upper throat relax. During breathing, inhalation and exhalation causes the soft tissues in the upper throat to vibrate creating the sound we identify as snoring. Sleep apnea results from a more pronounced obstruction of the upper air passage which results in a cessation of breathing. Severe cases of sleep apnea are life threatening should the individual fail to resume breathing. Lesser symptoms include excessive daytime drowsiness and increased blood pressure that can produce strokes and eventually, in extreme cases, cardiac arrest.

In some of these extreme cases, surgical correction is attempted to alleviate the symptoms of sleep apnea by a procedure such as a tracheotomy. Most patients would prefer a less extreme, non-invasive procedure such as an oral appliance. This has led to a proliferation of any number of mouthpiece type appliances designed to pull the mandible forward ensuring an adequate opening to permit sufficient ingress/egress of air to reduce or eliminate the problems associated with snoring and sleep apnea. Among those appliances which are adjustable to provide a variety of mandibular positions, most are difficult to adjust and require the intervention of a dentist. Further, none of the available devices takes into account the fact that the incisors typically open between 2 and 2½ times as far as the rear molars as the mandible pivots about its connection to the upper jaw. This results in ill-fitting appliances which fail to perform as well as they might. Some of the appliances do not permit lateral movement of one mouthpiece relative to the other. This can cause the jaw muscle to become aggravated, particularly for those patients who tend to grind their teeth during sleep.

The nocturnal oral airway dilator (NORAD) appliance of the present invention effectively deals with the problems of snoring and sleep apnea while overcoming the limitations of the prior art apparatus. The appliance of the present invention comprises a first mouthpiece element for engaging a wearer's teeth on an upper jaw, the first mouthpiece having an anterior portion and a pair of posterior portions; a second separate mouthpiece element for engaging a wearer's lower teeth on a mandible, the second mouthpiece having an anterior portion and a pair of posterior portions; a first pair of ramp surfaces, one on each of the posterior portions of the first mouthpiece element; a second pair of ramp surfaces, one on each of the posterior portions of the second mouthpiece element for engaging the first pair of ramp surfaces; whereby when the second mouthpiece element is adjusted so as to extend the wearer's mandible forward by an additional amount relative to the wearer's upper jaw, engagement between the first and second pair of ramp surfaces causes the mandible to be moved vertically away from the upper jaw by an additional amount.

A first plurality of lateral positional ribs are formed on the anterior portion of the first mouthpiece element and a second plurality of laterally extending positional ribs are formed on the anterior portion of the second mouthpiece element for engaging at least some of the first plurality of laterally extending ribs to adjustably position the second mouthpiece element longitdinally relative to the first mouthpiece element while permitting relative lateral movement between the first and second mouthpiece elements. Preferably, the first and second plurality of ribs each slope at identical angles, being ramped upwardly front to back at an angle greater than the slope on the first and second pairs of ramp surfaces. The ratio of the maximum height of the ribs to that of said first and second pairs of ramp surfaces are designed to mirror a opening differential between the wearer's front mouth opening and the wearer's rear mouth opening and most preferably has a value of between 2 and 2½.

The first and second mouthpiece elements are each made of two different bio-compatible, translucent plastic materials, a first plastic material with a Shore D hardness of about 30 and a softening point in the range between 120 and 180° F. and a second bio-compatible, translucent material having a Shore D hardness of at least 70 and which does not appreciably soften at temperatures below 200° F. The first plastic material is preferably ethylene vinyl acetate and the second plastic material is preferably an ethylene methyl acrylate co-polymer. The upper and lower mouthpieces will be color-coded so the wearer is clear about which is the upper and which is the lower mouthpiece.

Each pair of mouthpiece elements has a plurality of protrusions extending outwardly from each lateral portion. These protrusions are engageable by elastic bands which exert a force which simultaneously biases the lower mouthpiece element toward the upper mouthpiece element and exerts a forward bias on the lower mouthpiece element relative to the upper mouthpiece element.

Various other features, advantages, and characteristics of the present invention will become apparent after a reading of the following detailed description.

BRIEF DESCRIPTION OF THE DRAWINGS

The preferred embodiment(s) of the present invention are set forth in the drawings, like items bearing like reference numerals and in which.

DETAILED DESCRIPTION OF THE PREFERRED EMBODIMENT(S)

Figure 1:
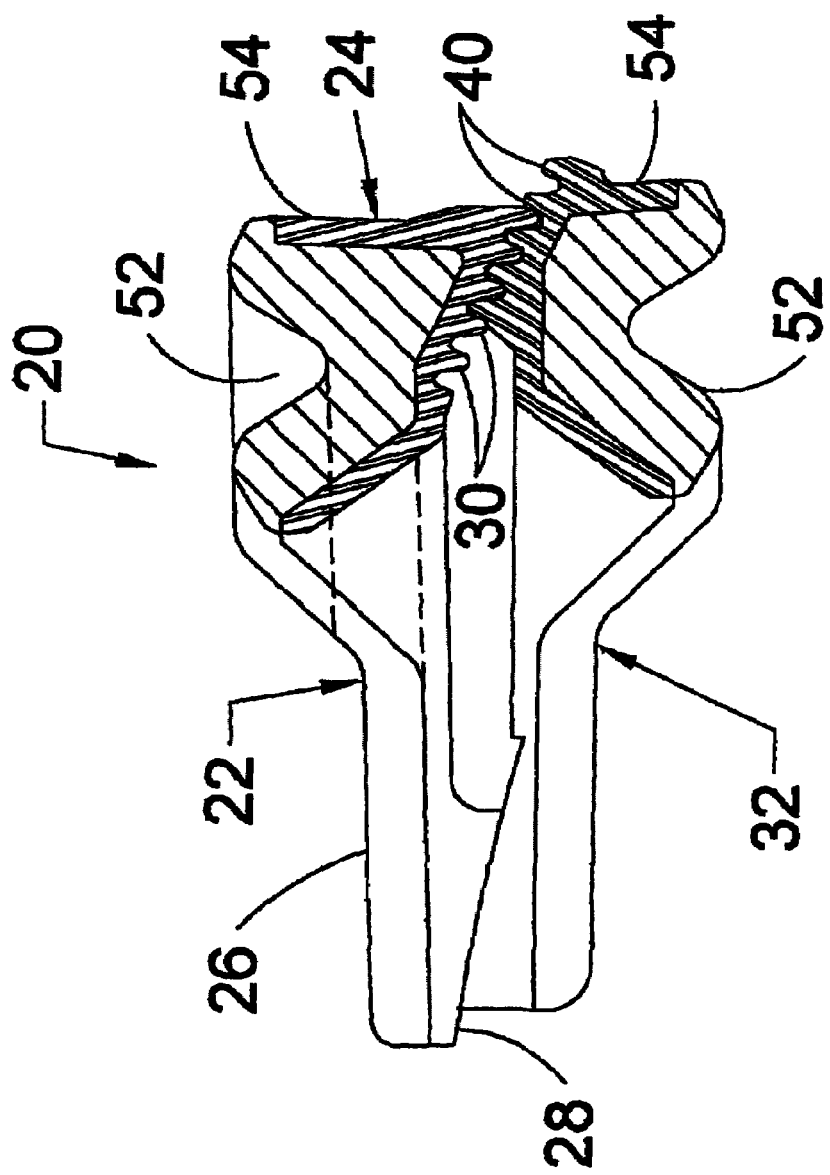
FIG. 1 is a cross-sectional side view of a first embodiment of the nocturnal oral airway dilator of the present invention.
Figure 2:
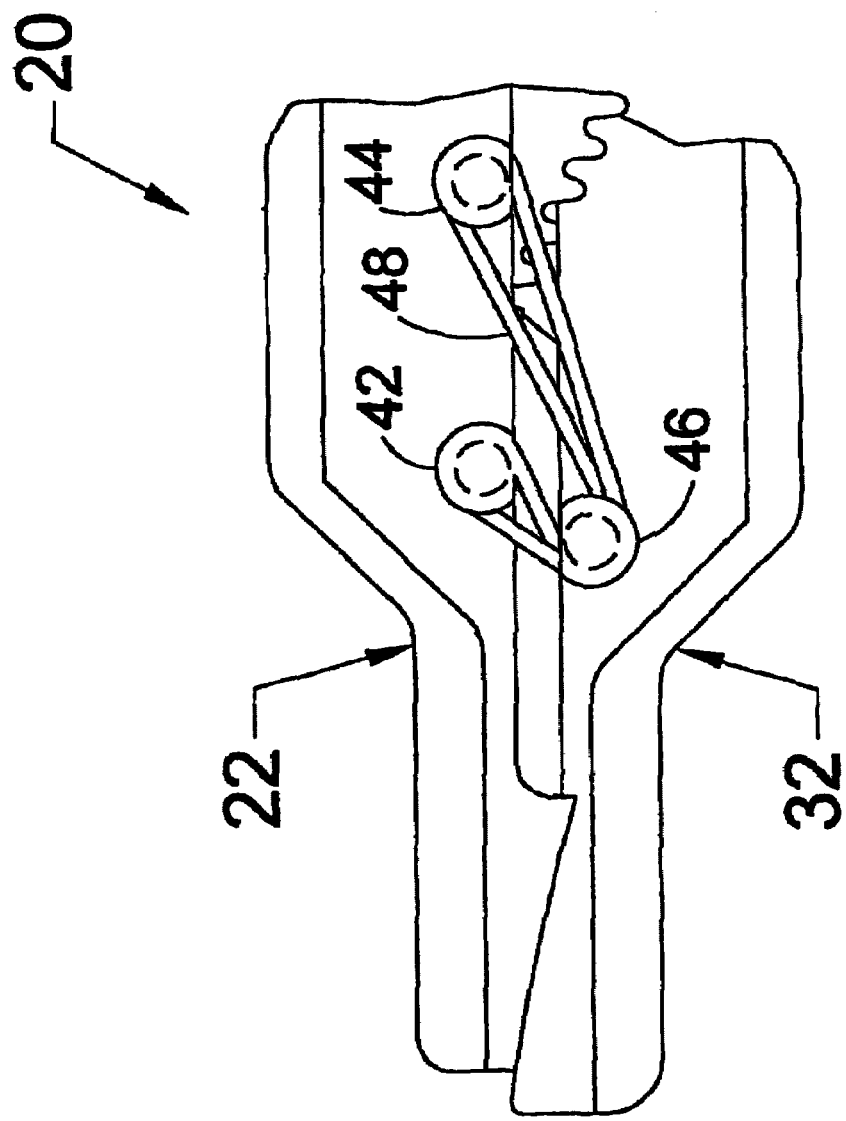
FIG. 2 is a side view of the first embodiment.

A first embodiment of the nocturnal oral airway dilator (NORAD) appliance of the present invention is shown in FIGS. 1 and 2 generally at 20. NORAD appliance 20 comprises a first mouthpiece element 22 for engaging a first set of teeth on the wearer's upper jaw and a second mouthpiece element 32 for engaging a second set of teeth on the wearer's mandible. First mouthpiece element 22 has an anterior portion 24 and two posterior portions 26. Each posterior portion is equipped with a radiused ramp surface 28 while the anterior portion 24 has a first plurality of laterally extending ribs 30.

Second mouthpiece element 32 has an anterior portion 34 with a second plurality of laterally extending ribs 40 for engaging the first plurality of ribs 30 on the first mouthpiece element 22. The two posterior portions 36 of second mouthpiece element 32 each have a complementarily radiused ramp surface 38 which engage the first pair of ramp surfaces 28. Ribs 30 and 40 slope upwardly at identical angles, front to back in mouthpiece elements 22 and 32, respectively. The angle on nibs 30 and 40 is greater than the slope on the ramp surfaces 28, 38. Preferably, the ratio of the maximum height on ribs 30, 40 to the maximum height on ramp surfaces 28, 38 mimics the differential of movement between incisors and molars and hence, the ratio is preferably in the range of between 2 and 2½.

Ribs 30 and 40 can engage one another in a plurality of configurations to provide a plurality of adjusted positions for the wearer's mandible relative to her/his upper jaw. The purpose of the NORAD appliance 20 is to pull the mandible forward relative to the upper jaw to keep the air passage open. The engagement between first (28) and second (38) pairs of ramp surfaces simultaneously increases the vertical spacing between upper and lower sets of teeth as the mandible is extended forward. Since engaged nibs 30 and 40 extend laterally, the wearer is free to adjust the position of her/his jaw during the night, avoiding aggravation of the jaw muscle that would potentially result if such movement were restricted.

First (22) and second (24) mouthpiece elements have a total of at least three laterally extending protrusions 42, 44, 46 extending from each side. Elastic bands 48 are woven about protrusions 42, 44, 46 to exert a force which simultaneously biases said mandible forward and toward the upper jaw. It is the relaxing of the muscles of the throat that result in the problems of snoring and sleep apnea. The NORAD appliance counteracts this slumping of the throat muscles reducing or eliminating these problems.

First (22) and second (24) mouthpiece elements are manufactured of two translucent plastic materials 52 and 54. The use of bio-compatible translucent plastics 52 and 54 enable the dentist to see the wearer's teeth during fitting of the appliance 20. The first plastic 52 preferably has a Shore D hardness of about 30 and a softening point in the 120 to 180° F. The second plastic material 54 preferably has a Shore D hardness of about 70 and will not appreciably soften at temperatures below 200° F. The low softening point of first plastic material 52 enables the plastic material 52 to fit snugly to the wearer's teeth through a process identified as "boil and bite" without subjecting the second plastic material 54 to the possibility of deformation. The mouthpiece elements 22 and 32 are immersed in boiling water to soften the first plastic material 52 and then, placed in the wearer's mouth to shape the material 52 to fit snugly about her/his teeth. Tests are being performed to determine the optimum materials for this application. At this time, the best mode of Applicant's appliance calls for the first plastic material 52 to be ethylene vinyl acetate and the second plastic material 54 to be an ethylene methyl acrylate co-polymer. Obviously, other plastic materials meeting the above criteria of bio-compatibility and Shore D hardness could be employed equally as well.

Figure 3A:
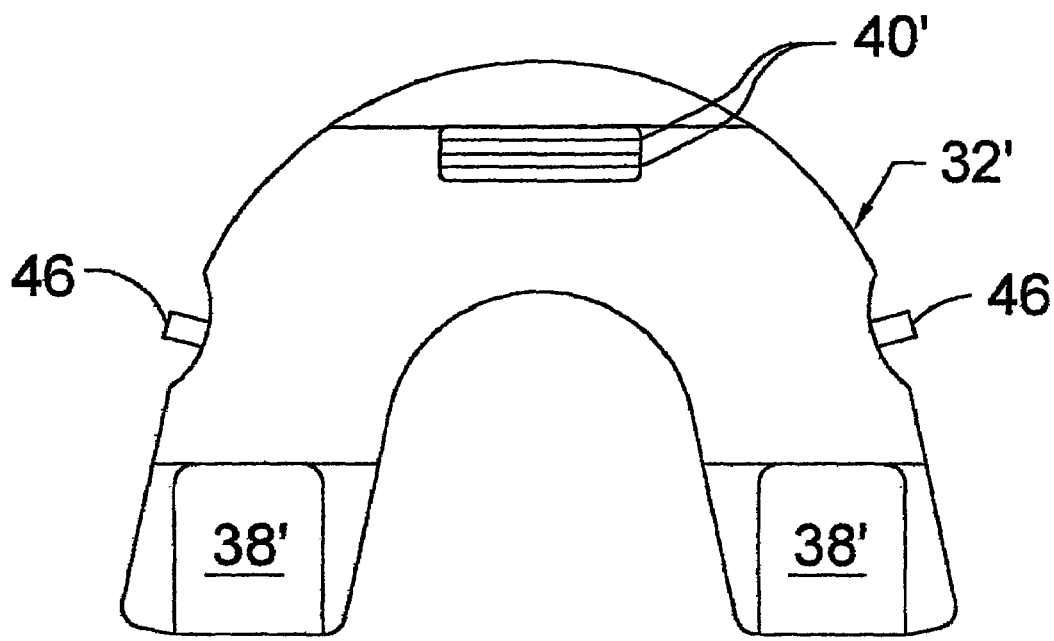
FIG. 3A is a top view of the lower mouthpiece of a second embodiment of the nocturnal oral airway dilator of the present invention.
Figure 3B:
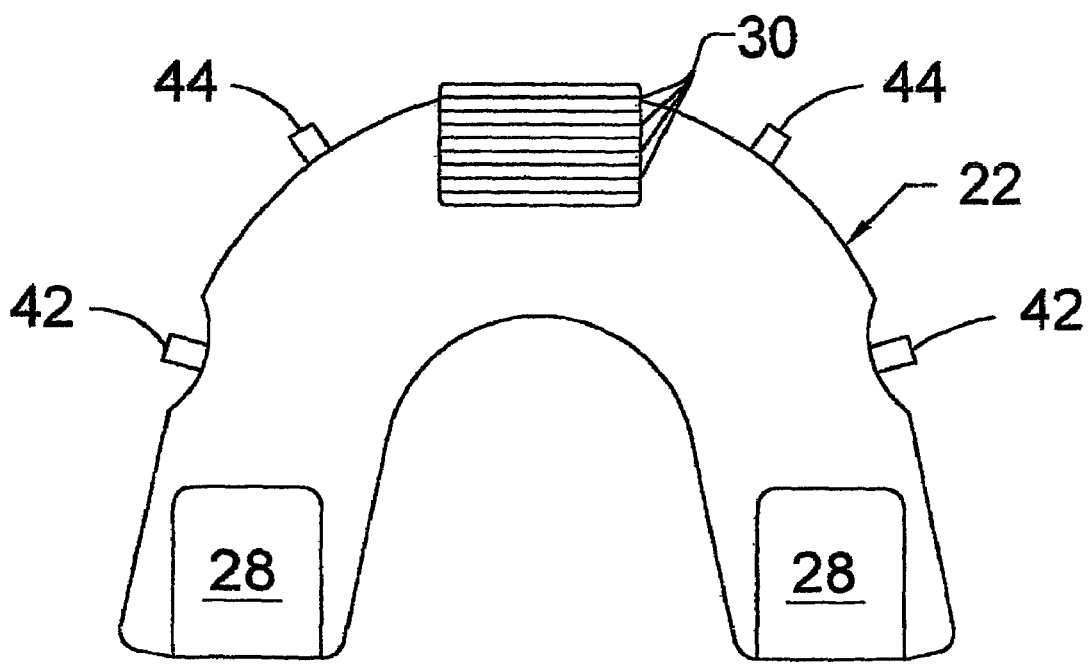
FIG. 3B is a bottom view of the upper mouthpiece of the first embodiment of the nocturnal oral airway dilator of the present invention.

First (22) and second (24) mouthpiece elements are depicted in FIGS. 1 and 2 as having equal numbers of ribs 30, 40. As shown in FIG. 3A in a second embodiment, lower mouthpiece element 32' is provided with only a pair of ribs 40'. This modification simplifies production without appreciably reducing the adjustment capabilities of appliance 20.

The NORAD appliance 20 may be fitted using the "boil and bite" technique and an initial relational positioning of second mouthpiece element 40 relative to first mouthpiece element 30 by engaging several of the second ribs 40 with first ribs 30 and the elastic bands 48 positioned about laterally extending protrusions 42, 44, 46 to exert a force providing simultaneously a forward bias on the wearer's mandible and a closing force drawing second mouthpiece element 32 toward first mouthpiece element 22. Should the NORAD appliance need adjusting to more effectively deal with the snoring/sleep apnea problem with which it is dealing, upon advice of the dentist, the wearer may adjust the appliance her/himself by repositioning ribs 40 relative to ribs 30.

Various changes, alternatives and modifications will become apparent to one of ordinary skill in the art following a reading of the foregoing specification. It is intended that all such changes, alternatives and modifications as fall within the scope of the appended claims be considered part of the present invention.

The invention claimed is:

1. A nocturnal oral airway dilator comprising
 a) a first mouthpiece element for engaging a wearer's teeth on an upper jaw, said first mouthpiece having an anterior portion and a pair of posterior portions;
 b) a second separate mouthpiece element for engaging a wearer's lower teeth on a mandible, said second mouthpiece having an anterior portion and a pair of posterior portions;
 c) a first pair of ramp surfaces, one on each of said posterior portions of said first mouthpiece element, said first ramp surfaces sloping from a minimum dimension toward said posterior portion and a maximum dimension toward said anterior portion;
 d) a second pair of ramp surfaces, one on each of said posterior portions of said second mouthpiece element for engaging said first pair of ramp surfaces, said second ramp surfaces sloping from a maximum dimension toward said posterior portion and a minimum dimension toward said anterior portion;
whereby when said second mouthpiece element is adjusted so as to extend the wearer's mandible forward by an additional amount relative to the wearer's upper jaw, engagement between said first and second pair of ramp surfaces causes the mandible to be moved vertically away from the upper jaw by an additional amount.

2. The nocturnal oral airway dilator of claim 1 further comprising a first plurality of laterally extending positional ribs on said anterior portion of said first mouthpiece element and a second plurality of laterally extending positional ribs on said anterior portion of said second mouthpiece element for engaging at least some of said first plurality of laterally extending ribs to adjustably position said second mouthpiece element longitudinally relative to said first mouthpiece element while permitting relative lateral movement between said first and second mouthpiece elements.

3. The nocturnal oral airway dilator of claim 2 wherein said first and second plurality of ribs each slope at identical angles.

4. The nocturnal oral airway dilator of claim 3 wherein said identical angles ramp upwardly front to back at an angle greater than the slope on said first and second pairs of ramp surfaces.

5. The nocturnal oral airway dilator of claim 4 wherein a ratio between a maximum height of said plurality of ribs to a maximum height of said ramp surfaces mimics a ratio of opeing distances between a patients incisors and molars.

6. The nocturnal oral airway dilator of claim 5 wherein said identical angles have a ratio with respect to said ramp angles in a range of between 2 and 2½.

7. The nocturnal oral airway dilator of claim 1 wherein said first and second mouthpiece elements are each made of biocompatible, translucent plastic to enable a dentist installing said first and second mouthpiece elements to see the wearer's teeth with said first and second mouthpiece elements in their installed positions.

8. The nocturnal oral airway dilator of claim 7 wherein said first and second mouthpiece elements are color coded to identify which is for engagement with the upper jaw and which is for engagement with the mandible.

9. The nocturnal oral airway dilator of claim 8 wherein said first and second mouthpiece elements are made of a first plastic material having a Shor durometer of about 30 and a softening point in the range of 120 to 180° F.

10. The nocturnal oral airway dilator of claim 9 wherein said first biocompatible, translucent plastic is preferably ethylene vinyl acetate.

11. The nocturnal oral airway dilator of claim 9 wherein said first and second mouthpiece elements are further made of a second plastic material having a Shor durometer in excess of 70 and which will not appreciably soften at temperatures below 200°.

12. The nocturnal oral airway dilator of claim 10 wherein said second plastic material is an ethylene methyl acrylate co-polymer.

13. The nocturnal oral airway dilator of claim 1 further comprising at least three laterally extending protrusions on each pair of mouthpiece elements, elastic band means for engaging each of said at least three laterally extending protrusions in a manner to exert a force which simultaneously biases said mandible forward and toward the upper jaw.

14. The nocturnal oral airway dilator of claim 1 wherein said first and second mouthpiece elements are configured to maintain a ratio of distances between anterior sets of teeth and posterior sets of teeth in a range between 2 and 2.5.

15. A nocturnal oral airway dilator comprising
    a) first mouthpiece element for engaging a wearer's teeth on an upper jaw, said first mouthpiece having an anterior portion and a pair of posterior portions;
    b) second separate mouthpiece element for engaging a wearer's lower teeth on a mandible, said second mouthpiece having an anterior portion and a pair of posterior portions;
    c) a first set of positioning ribs on said anterior portion of said first mouthpiece element extending laterally relative thereto;
    d) a second set of positioning ribs on said anterior portion of said second mouthpiece element extending laterally relative thereto for engaging said first set of ribs at a plurality of longitudinal positions to restrict relative longitudinal movement while permitting relative lateral movement;
    e) elastic band means engaging protrusions on each lateral portion of said first and second mouthpiece elements to impart a force which simultaneously draws said second mouthpiece element toward said first mouthpiece and exerts a forward bias on said second mouthpiece element relative to said first mouthpiece element;

wherein said first plurality of ribs slopes front to back with the forward most ribs being longer than the rearward most ribs.

16. The nocturnal oral airway dilator of claim 15 further comprising a first pair of ramp surfaces on each side of a posterior portion of said first mouthpiece element, said first ramp surfaces sloping from a minimum dimension toward said posterior portion and a maximum dimension toward said anterior portion and a second pair of ramp surfaces on each side of a posterior portion of said second mouthpiece element for engaging said first pair of ramp surfaces, said second ramp surfaces sloping from a maximum dimension toward said posterior portion and a minimum dimension toward said anterior portion, whereby when said second mouthpiece element is adjusted so as to extend the wearer's mandible forward by an additional amount relative to the wearer's upper jaw, engagement between said first and second pair of ramp surfaces causes the mandible to be moved vertically away from the upper jaw by an additional amount.

17. The nocturnal oral airway dilator of claim 15 wherein said second plurality of ribs slopes front to back with the forward most ribs being shorter than the rearward most ribs.

18. The nocturnal oral airway dilator of claim 15 wherein said first and second mouthpiece elements are configured to maintain a ratio of distance between anterior sets of teeth and posterior sets of teeth in a range between 2 and 2.5.

19. The nocturnal oral airway dilator of claim 15 wherein said first and second mouthpiece elements are each made of a first plastic material having a Shor durometer of about 30 and a softening point in the range between 120 and 180° F. and a second plastic material having a Shor durometer of at least 70, said second plastic not appreciably softening at temperatures below 180° F.

\* \* \* \* \*